United States Patent
Clark et al.

(10) Patent No.: US 11,562,827 B2
(45) Date of Patent: Jan. 24, 2023

(54) NEGATIVE INFERENCES IN MACHINE LEARNING TREATMENT SELECTION

(71) Applicant: International Business Machines Corporation, Armonk, NY (US)

(72) Inventors: Adam Clark, Mantorville, MN (US); Richard J. Stevens, Monkton, VT (US); Fernando Suarez Saiz, Armonk, NY (US); Eric W. Will, Rochester, MN (US); Mark Gregory Megerian, Rochester, MN (US); Thomas J. Eggebraaten, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 976 days.

(21) Appl. No.: 16/280,331

(22) Filed: Feb. 20, 2019

(65) Prior Publication Data

US 2020/0265954 A1 Aug. 20, 2020

(51) Int. Cl.
*G16H 50/20* (2018.01)
*G06N 20/00* (2019.01)
(Continued)

(52) U.S. Cl.
CPC ......... *G16H 50/20* (2018.01); *G06F 16/9024* (2019.01); *G06N 20/00* (2019.01); *G16H 10/60* (2018.01); *G16H 20/00* (2018.01)

(58) Field of Classification Search
CPC ........ G16H 50/20; G16H 10/60; G16H 20/00; G16H 70/60; G16H 50/70; G06F 16/288;
(Continued)

(56) References Cited

U.S. PATENT DOCUMENTS

| 7,370,023 B1 * | 5/2008 | Forsythe .................. G06N 5/02 706/14 |
| 7,991,733 B2 | 8/2011 | Mons et al. |

(Continued)

OTHER PUBLICATIONS

Liang Yao etal, "Incorporating Knowledge Graph Embeddings into Topic Modeling," Proceedings of the Thirty-First AAA! Conference on Arifficial Inteligence (AAAI-17), Year: 2017, pp. 3119-3126 (Year: 2017).*

(Continued)

*Primary Examiner* — James N Fiorillo
(74) *Attorney, Agent, or Firm* — Patterson + Sheridan, LLP (57) ABSTRACT

Method and apparatus for performing feature engineering using negative inferences are provided. One example method generally includes identifying a plurality of concepts and analyzing a corpus of documents to determine a first co-occurrence rate for a first concept and a second concept in the plurality of concepts. The method further includes analyzing the corpus of documents to determine a second co-occurrence rate for the second concept and at least a third concept of a set of concepts related to the first concept and determining an inverse relationship between the second concept and the third concept. The method further includes generating test data for training a machine learning model including a negative inference between the second concept and the third concept and training the machine learning model using the test data.

20 Claims, 4 Drawing Sheets

(51) Int. Cl.
   *G06F 16/901* (2019.01)
   *G16H 10/60* (2018.01)
   *G16H 20/00* (2018.01)

(58) Field of Classification Search
   CPC .............. G06F 16/901; G06F 16/9024; G06F 16/9027; G06F 11/3608; G06N 20/00; G06N 5/02; G06N 99/005; H04L 67/10
   USPC .......................................................... 706/12
   See application file for complete search history.

(56) References Cited

U.S. PATENT DOCUMENTS

| | | | | |
|---|---|---|---|---|
| 8,337,408 | B2* | 12/2012 | Wariar | A61B 5/16 600/300 |
| 11,087,882 | B1* | 8/2021 | Perlin | H04L 67/565 |
| 11,113,175 | B1* | 9/2021 | Adamo | G06F 40/216 |
| 2006/0270918 | A1* | 11/2006 | Stupp | G16H 10/20 128/920 |
| 2014/0095206 | A1* | 4/2014 | Fung | G16H 50/30 705/3 |
| 2014/0149132 | A1* | 5/2014 | DeHaan | G16H 70/20 705/2 |
| 2014/0214451 | A1* | 7/2014 | Fung | G16H 10/60 705/3 |
| 2014/0337306 | A1 | 11/2014 | Gramatica | |
| 2015/0278459 | A1 | 10/2015 | Yui et al. | |
| 2015/0379430 | A1* | 12/2015 | Dirac | G06N 20/00 706/12 |
| 2016/0048655 | A1* | 2/2016 | Maitra | G16H 70/40 705/3 |
| 2018/0260442 | A1* | 9/2018 | Vaidhyanathan | G06F 16/285 |
| 2018/0285769 | A1* | 10/2018 | Wu | G06N 20/00 |
| 2018/0336242 | A1* | 11/2018 | Llaves | G06N 20/00 |
| 2018/0336272 | A1* | 11/2018 | Garcia Santa | G06F 40/30 |
| 2020/0081882 | A1* | 3/2020 | Cheriton | G06F 16/9024 |
| 2020/0118662 | A1* | 4/2020 | Norman | C07K 14/61 |
| 2022/0035728 | A1* | 2/2022 | Muras | G06F 40/30 |

OTHER PUBLICATIONS

Rotmensch et al, "Learning a Health Knowledge Graph from Electronic Medical Records," Scientific Reports, Received: Mar. 3, 2017 | Accepted Jun. 1, 2017| Published Online: Jul. 20, 2017 | 11 pages.

Authors et. al.: Disclosed Anonymously, "A Process and its Application for the Construction of Residual Quantitative Medical Models to Assess the Adherence, Effectiveness, and Accuracy of Doctors' Treatment Behaviors," IP.com No. IPCOM000248367D | IP.com Electronic Publication Date: Nov. 21, 2016 | 4 pages.

Authors et. al.: Disclosed Anonymously, "OptCare—A system for for personalizing clinical care pathways," IP.com No. IPCOM000244976D | IP.com Electronic Publication Date: Feb. 4, 2016 | 13 pages.

Micael Derelöv, "On Evaluation of Design Concepts," Linköping studies in science and technology. Dissertations, No. 1273 | ISBN 978-91-7393-536-4 | ISSN 0345-7524 | 2009 | 136 pages.

Authors et. al.: Disclosed Anonymously, "Disease Relevancy Evaluation for a Corpus of Evidence," IP.com No. IPCOM000234117D | IP.com Electronic Publication Date: Jan. 13, 2014 | 4 pages.

Liang Yao et al., "Incorporating Knowledge Graph Embeddings into Topic Modeling," Proceedings of the Thirty-First AAAI Conference on Artificial Intelligence (AAAI-17), Year: 2017, pp. 3119-3126.

\* cited by examiner

NEGATIVE INFERENCES IN MACHINE LEARNING TREATMENT SELECTION

BACKGROUND

The present invention relates to machine learning-enabled treatment selection, and more specifically, to feature engineering for machine learning-enabled treatment selection.

As machine learning techniques have advanced, the use of machine learning in different applications has greatly increased. One way in which machine learning has improved over time is through the use of feature engineering. Typically, feature engineering may be performed prior to training a machine learning model in order to improve the data used for training, and ultimately the output of the machine learning model once trained. Feature engineering may be either automated or manual.

Existing feature engineering has some limitations, however. One such limitation is the lack of complex logical inferences in automated feature engineering. Manual feature engineering may be able to include such inferences, however manual feature engineering is time consuming, expensive, and in general impractical given the vast number of potential inferences across all potential attributes or concepts in a data set. Therefore, systems and methods are needed which extend the capabilities of conventional automated feature engineering.

SUMMARY

Certain embodiments provide a method for performing feature engineering using negative inferences. The method generally includes identifying a plurality of concepts and analyzing a corpus of documents to determine a first co-occurrence rate for a first concept and a second concept in the plurality of concepts, wherein the first co-occurrence rate relates to a number of times the first and second concepts were identified together in a same context. The method further includes, upon determining that the first co-occurrence rate exceeds a predefined threshold, analyzing the corpus of documents to determine a second co-occurrence rate for the second concept and at least a third concept of a set of concepts related to the first concept and, upon determining that second co-occurrence rate is below the predefined threshold, determining an inverse relationship between the second concept and the third concept. The method further includes generating test data for training a machine learning model including a negative inference between the second concept and the third concept and training the machine learning model using the test data.

Another embodiment includes a computing device comprising a processor and memory including instructions that cause the computing device to perform the method for feature engineering using negative inferences described above. Still another embodiment includes non-transitory computer readable medium comprising instructions, which when executed by a processor of a computing device, cause the computing device to perform the method for feature engineering using negative inferences described above.

DETAILED DESCRIPTION

Negative inferences in machine learning may be helpful in a variety of contexts or applications. One such application is the use of machine learning models to aid physicians in selecting treatments for patients with various medical conditions. In general, such machine learning models are trained using a variety of data, such as medical studies, patient histories and known treatment success rates, to select a treatment (or multiple treatments) for a particular patient. The physician using the machine learning model can then use the model's recommended treatment in making a final treatment selection. In machine learning-enabled treatment selection, an example of a negative inference for treatment purposes can be found in cancer diagnosis. In particular, if a cancer patient is known to be "metastatic" then it can be inferred that the cancer patient has stage 4 cancer. Such an inference may be implemented in current machine learning-enabled treatment selection. However, the opposite inference, that if a cancer patient is known to be not metastatic, then the cancer patient must not have stage 4 cancer (that is, the cancer patient has stage 1, 2 or 3 cancer) is more difficult to implement into automatic feature engineering.

In order to incorporate negative inferences into automatic feature engineering a method employing co-occurrence rates may be used. In particular, based on co-occurrence rates a connection between a first concept (e.g., stage 4 cancer) and a second concept (e.g., metastasis) may be established. If it can also be established that there is no connection between the second concept and a third concept (e.g., stage 3 cancer) related to the first concept, then an inverse relationship between the third concept and the second concept can be established. That is, it can be established that while one can infer the first concept (stage 4 cancer) from the second concept (metastasis) (e.g., if a patient has stage 4 cancer he is metastatic), or vice versa, one can also rule out the possibility of the third concept (stage 3 cancer) from the presence of the second concept (metastasis) (e.g., if a patient is metastatic he does not have stage 3 cancer), or vice versa.

Using the above method employing co-occurrence rates, it is possible for an automated feature engineering system to determine inverse relationships between concepts, which can be used to deduce negative inferences in situations involving the concepts, using the same data as is currently used in performing conventional feature engineering. Test data produced by use of such improved feature engineering techniques (e.g., with negative inference capability) may improve the quality of resulting machine learning models.

Figure 1:
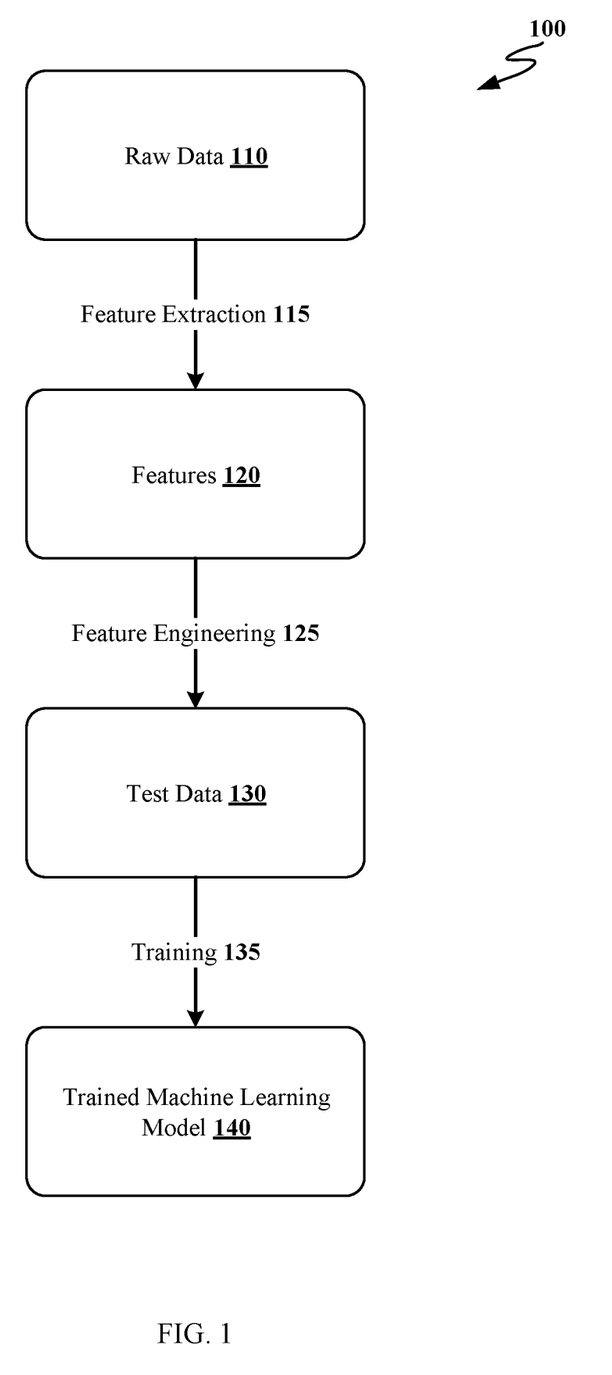
FIG. 1 depicts an example data pipeline in a machine learning process.

FIG. 1 depicts an example data pipeline 100 for machine learning. Data pipeline 100 demonstrates the process by which raw data 110 is used in the training of trained machine learning model 140.

Data pipeline 100 begins with raw data 110, which may be obtained from a variety of sources, depending on the application for which the trained machine learning model 140 will be used. As one example, for medical treatment selection (or other medical-related applications), raw data 100 may include documents such as medical studies, documents related to clinical trials, drug labels, treatment guidelines, patient results, patient medical records, or other medical documents. In some cases raw data 110 may also be referred to as a corpus of literature or a corpus of documents.

At 115, feature extraction is performed on raw data 110 to produce features 120. In general, feature extraction is intended to isolate meaningful aspects of raw data 110, and to remove irrelevant or meaningless aspects of raw data 110, such as punctuation or other unintelligible information. Feature extraction also includes formatting the meaningful aspects of raw data 110 into a computer-readable format, such as, for example, numerical or vector representations of words and other document content. Feature extraction may be performed manually or automatically. However, as machine learning accuracy tends to benefit from increased test data size, and manual feature extraction is impractical for use on large amounts of raw data, automatic feature extraction may be preferable.

Features 120 are the product of feature extraction, and typically include computer-readable representations of raw data 110.

At 125, feature engineering may be performed on features 120 to produce test data 130 out of features 120. Feature engineering tends to improve the quality of test data used for training, and by extension the accuracy and functionality of a trained machine learning model. Typical feature engineering may include augmenting features 120 with information that may be inferred from the available information of features 120, such as by identifying a single variable (or data point) that is as informationally valuable as two other variables. However, conventional feature engineering does not provide for determining negative inferences. Use of negative inferences in feature engineering is discussed in further detail below.

Test data 130 can be used in the training of machine learning models. Typically, test data 130 is provided to a machine learning algorithm (not shown), and output from the machine learning algorithm is repeatedly refined to produce a fully trained model, shown as trained machine learning model 140. The functionality of trained machine learning model 140, as well as the accuracy of the output of trained machine learning model 140, depends on the quality and quantity of test data 130. As such, improvements to the steps of feature extraction and feature engineering ultimately result in improvements to the functioning of machine learning models.

Figure 2:
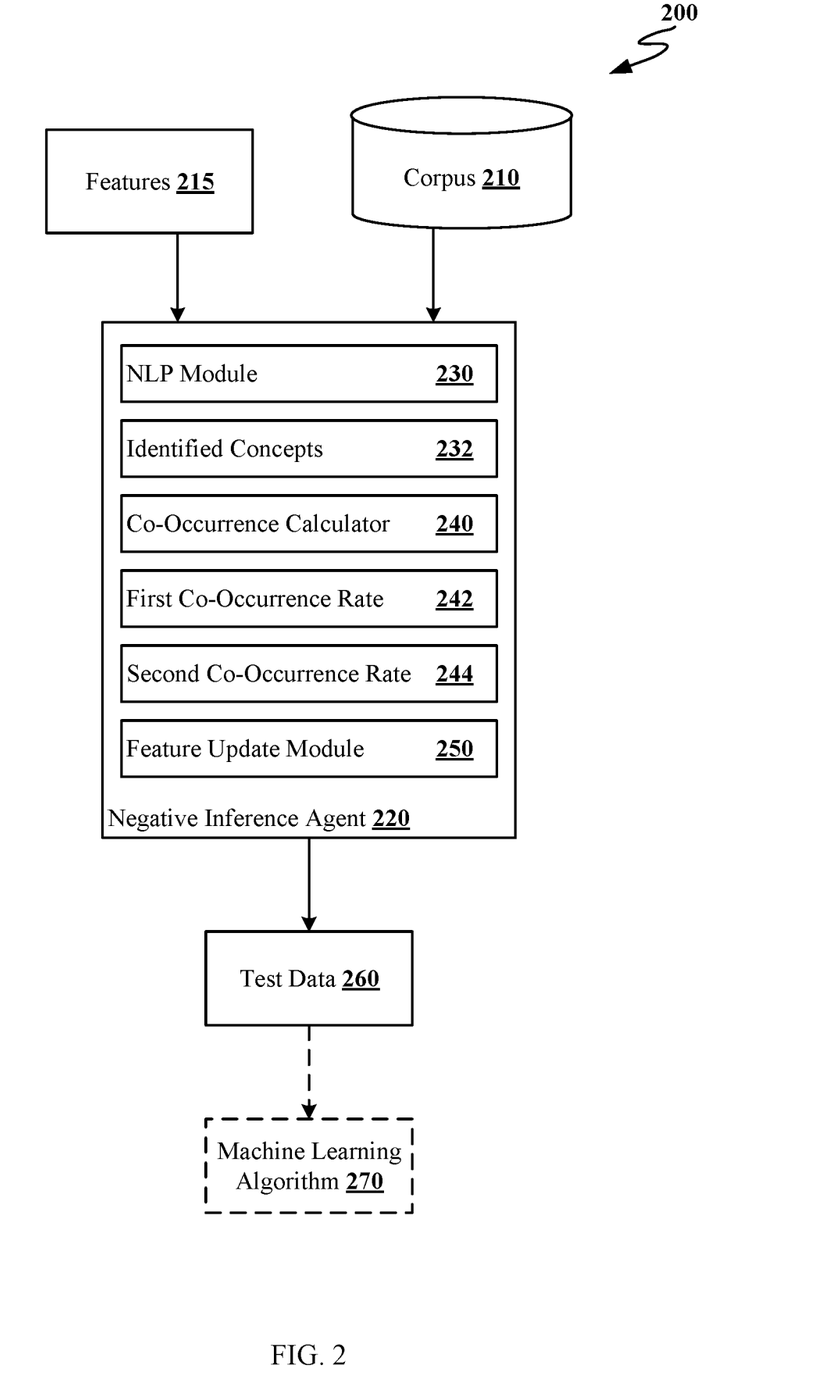
FIG. 2 depicts an example data pipeline for feature engineering including negative inferences.

FIG. 2 depicts an example data pipeline 200 for feature engineering including negative inferences.

In general, data pipeline 200 serves to enhance features 215 into test data 260. In data pipeline 200, negative inferences can be identified using corpus 210. Corpus 210 may include, for example, digitized documents or other pieces of information. If data pipeline 200 is used to perform feature engineering for machine learning-enabled treatment selection, corpus 210 may include a wide array of medical documents, as described above with respect to FIG. 1.

In this example, negative inference agent 220 is a software module or routine executing on a computing device (or cloud computing system) within data pipeline 200. Negative inference agent 220 includes a number of software subroutines and data files that can be used to augment features 215 with negative inferences. In particular, negative inference agent 220 includes natural language processing (NLP) module 230, identified concepts 232, co-occurrence calculator 240, first co-occurrence rate 242, second co-occurrence rate 244, and feature update module 250.

NLP module 230 is a software subroutine of negative inference agent 220 that accesses corpus 210 and performs various NLP tasks to identify concepts with the corpus of literature. NLP tasks may include preprocessing tasks such as tokenization (generating smaller numerical "tokens" to represent parts of speech) and normalization (e.g., stemming, lemmatization, removing stop words or replacing word variants with a standardized word). In general, NLP module 230 identifies various concepts represented in corpus 210, and stores the result as identified concepts 232. For the purposes of this example, identified concepts 232 includes at least a first identified concept, a second identified concept, and a set of concepts related to the first identified concept. Initially, identified concepts 232 may not include any indication of relation or relevancy between concepts. As discussed below, concept relationships can be estimated by use of co-occurrence rates.

Co-occurrence calculator 240 is a software subroutine of negative inference agent 220 that calculates frequencies of co-occurrence between identified concepts 232. In general, co-occurrence calculator 240 accesses corpus 210 to determine the number of co-occurrences of concepts in the corpus of literature. For example, in digitized text, a co-occurrence may include mention of two concepts within fifty words of one another, although different measures of proximity (e.g., more or less words apart, presence on a particular page of a document or presence within a paragraph or other subsection of a document) can be used. Co-occurrence rates of words (or concepts) indicate a likely relationship between the co-occurring words (or concepts). Co-occurrence calculator 240 may calculate the co-occurrence rates between one concept and another, (e.g., how frequently does concept "A" co-occur with concept "B").

In this example, first co-occurrence rate 242 is the output of co-occurrence calculator 240 when searching for co-occurrences of the first concept and the second concept of identified concepts 232. In general, first co-occurrence rate 242 may be compared to a predetermined threshold to determine relevancy between the first concept and the second concept. For example, if two concepts co-occur at least 20% of the time either occurs in a document, those two concepts may be considered related for the purposes of negative inference agent 220. Notably, 20% is one example, and the predetermined threshold may vary based on implementation, underlying data characteristics, etc. In this example, first co-occurrence rate 242 exceeds the predetermined threshold, so the first concept and the second concept are determined to be related.

Second co-occurrence rate 244 is the output of co-occurrence calculator 240 when searching for co-occurrences of the second concept and at least one concept of a set of concepts related to the first concept (a third concept). In general, the set of related concepts may have been previously identified by comparisons of different concepts to the first concept by co-occurrence calculator 240, or by use of a knowledge graph, as described in further detail below.

For example, if the first concept is "stage 4 cancer", then the set of related concepts may include "stage 1 cancer," "stage 2 cancer," and "stage 3 cancer." Using a similar process as described above, co-occurrence calculator 240 searches corpus 210 to identify the co-occurrence rate of the second concept and the third concept, outputting second co-occurrence rate 244 as a result. In this example, second co-occurrence rate 244 falls below the predetermined threshold, so the second concept and the third concept are determined to not be related. This allows negative inference agent 220 to further determine an inverse relationship between the second concept (e.g., metastasis) and the third concept (e.g., stage 1 cancer). That is, negative inference agent 220 can establish an inverse relationship between "stage 1 cancer"

and "metastasis." This can be done because of the previous determination that the first concept ("stage 4 cancer") is related to both "metastasis" and "stage 1 cancer."

Following the determination of the inverse relationship between the second concept and the third concept, feature update module 250 may add the inverse relationship to test data 260. Feature update module 250 is a software subroutine of negative inference agent 220 that adds negative inferences determined from co-occurrence data to features 215. In general, feature update module 250 may, depending on the number of inverse relationships between concepts that can be identified, add a plurality of negative inferences to test data 260. There after, test data 260 can be used to train a machine learning model.

Test data 260 can then be provided to machine learning algorithm 270 as training data. Machine learning algorithm 270 may then be iteratively trained using test data 260, and the result of such training is a trained machine learning model. Because here the machine learning model is trained with the addition of negative inference-derived features, the machine learning model may have improved predictive capabilities compared to machine learning models trained without the additional features.

For example, if used in treatment selection, the machine learning model may be able to determine, based on knowledge that a patient has stage 1 cancer, that the patient is not metastatic and thus certain metastasis-related treatments could be ruled out. Currently, such negative inferences are not made by machine learning models.

In some embodiments, data pipeline 200 and/or trained machine learning models may make use of one or more knowledge graphs. For example, a knowledge graph may be configured as a multi-dimensional representation of the medical consensus as to relative efficacies of any number of therapies, with respect to any combination of particular cohorts and outcomes.

In some embodiments, outcomes types are associated with a predefined hierarchy. That is, some outcomes (e.g., progression-free survival) may be considered more important than other outcomes (e.g., side effects), and therefore be weighted more heavily when aggregating the relative efficacies with respect to each outcome in order to determine an overall relative efficacy (e.g., an overall optimal or best therapy, with respect to all outcomes). In such an embodiment, the ranking or scoring of the therapies may take into account the relative efficacies, as well as the importance or weight of the particular outcome. That is, although a first therapy may be the best with respect to side effects, it may be given a lower score than a second therapy that is better with respect to survival.

In some embodiments, a knowledge graph can be generated based on the determined relationships extracted from one or more published documents. For example, in one embodiment, each node in the knowledge graph corresponds to a particular therapy, and each edge corresponds to one or more as a relative efficacy structures (RESs). In this way, the knowledge graph can be interrogated or searched to identify optimal treatment options for a given patient, based on a tremendous variety of medical literature.

In some embodiments a knowledge graph may be utilized, rather than co-occurrence rates, to determine the set of concepts related to the first concept, such as by identifying edges from a node representing the first concept. In such embodiments, in addition to performing feature engineering using determined inverse relationships, the knowledge graph can also be updated to reflect the determined inverse relationships, such as by adding a negative edge (representing an inverse relationship) between nodes representing the second and third concepts.

Figure 3:
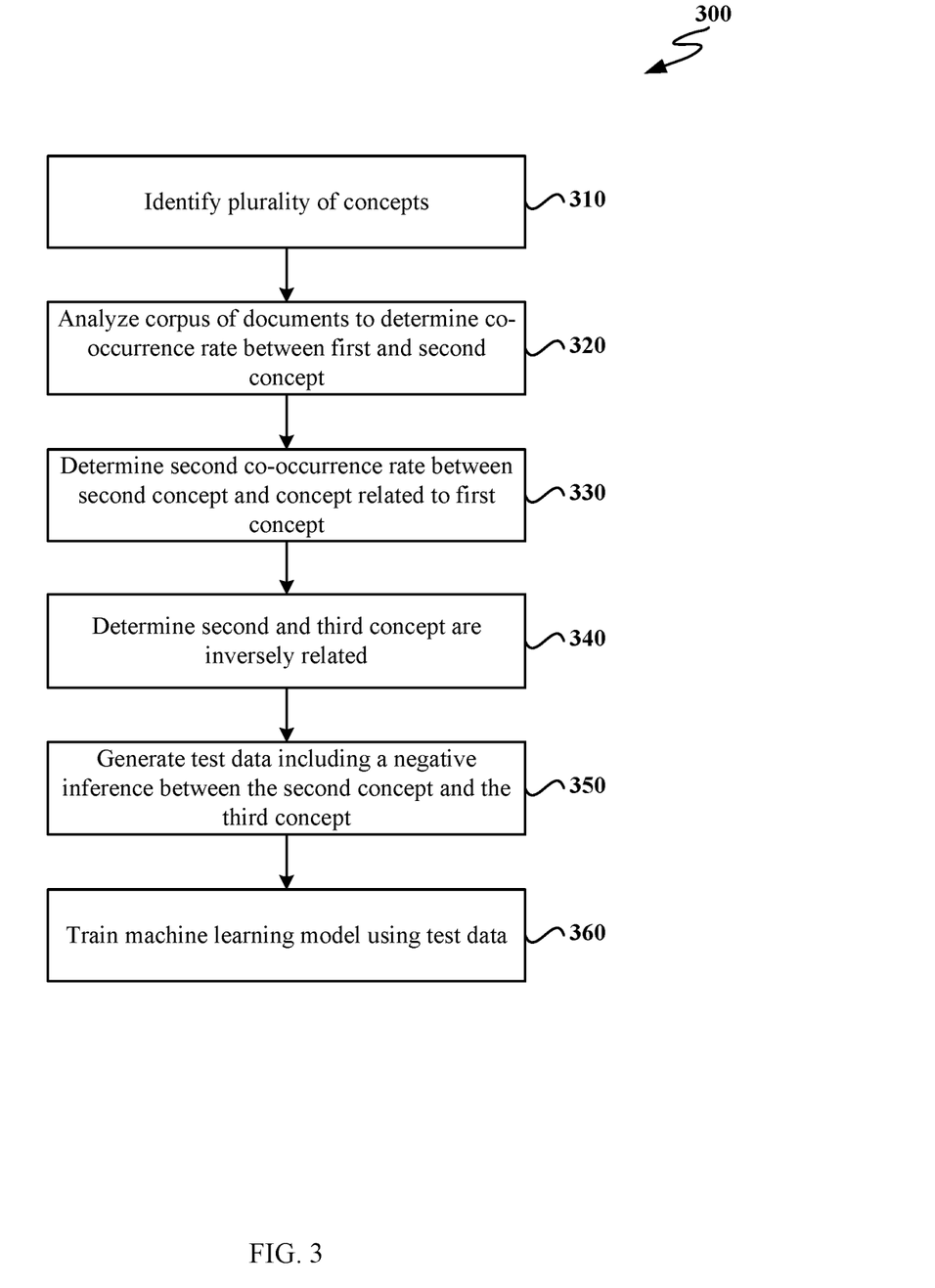
FIG. 3 is a flow diagram of an example method for identifying a negative inference based on two concepts.

FIG. 3 is a flow diagram of an example method 300 for identifying a negative inference based on two concepts. Method 300 may be performed by a computing device executing a negative inference agent, such as negative inference agent 220 of FIG. 2.

Method 300 begins at 310, where the computing device identifies a plurality of concepts. Identifying the plurality of concepts may be performed, for example, by analyzing a corpus of documents or by inspecting a knowledge graph. The plurality of concepts may vary depending on the context of use for method 300. For example, if method 300 is used in machine learning-enabled treatment selection, the concepts may relate to a variety of patient characteristics, medical conditions, or other information relevant to diagnosis and/or treatment selection.

At 320, the computing device analyzes a corpus of documents to determine first co-occurrence rate for a first and a second concept in the plurality of concepts. The first co-occurrence rate relates to a number of times the first and second concepts were identified together in a same context. For example, as discussed above, the same context may include proximity of the first and second concepts within a particular document.

At 330, upon determining that the first co-occurrence rate exceeds a predefined threshold, the computing device determines a second co-occurrence rate for the second concept and at least a third concept of a set of concepts related to the first concept. The predefined threshold may be any arbitrary value representing a level of confidence that co-occurrence in not merely coincidental. For example, 1% co-occurrence may be merely incidental, while 20% co-occurrence likely indicates an actual relationship between the concepts. The set of concepts related to the first concept may correspond to a possible value for the first concept. For example, if the first concept is "cancer" the related concepts may be "stage 1," "stage 2," "stage 3," and "stage 4." The set of related concepts may be identified by use of co-occurrence of the concepts or by use of positive edges of the knowledge graph. That is, two nodes in the knowledge graph connected by a positive edge are positively (or, directly) related.

At 340, upon determining that second co-occurrence rate is below the predefined threshold, the computing device determines an inverse relationship between the second concept and the third concept. As discussed above, the inverse relationship can be used to make negative inferences relative to the second concept and the third concept, such as that the presence of the second concept rules out the third concept, or vice versa.

At 360, the computing device generates test data including a negative inference between the second concept and the third concept. For example, the test data may include an indication that the presence of the second concept should rule out a conclusion including the third concept, and vice versa. In general, 360 is a feature engineering operation.

At 360, the computing device trains a machine learning model using the test data generated at 360. As the test data includes the negative inference between the second concept and the third concept, subsequent function of the machine learning model trained is improved, at least with respect to output of the machine learning model related to the second concept or the third concept.

In some examples of method 300, the first concept and the second concept are associated with medical conditions. In such examples, the machine learning model may used to perform treatment selection for a patient based in part on medical conditions of the patient.

In some cases, method 300 further includes, upon determining that a first patient is associated with the second concept, determining that the first patient is not associated with the third concept.

In some embodiments of method 300, determining the set of related concepts for the first concept comprises analyzing a knowledge graph, wherein the knowledge graph includes the plurality of concepts and a plurality of identified connections among the plurality of concepts. In the knowledge graph the plurality of concepts may be represented by nodes in the knowledge graph, and the plurality of identified connections may be represented by edges connecting the nodes.

In such embodiments, method 300 further includes updating the knowledge graph based on determining that the second concept and the first related concept are inversely related. Further, in such embodiments, updating the knowledge graph comprises adding a negative connection between the second concept and the first related concept in the knowledge graph.

Figure 4:
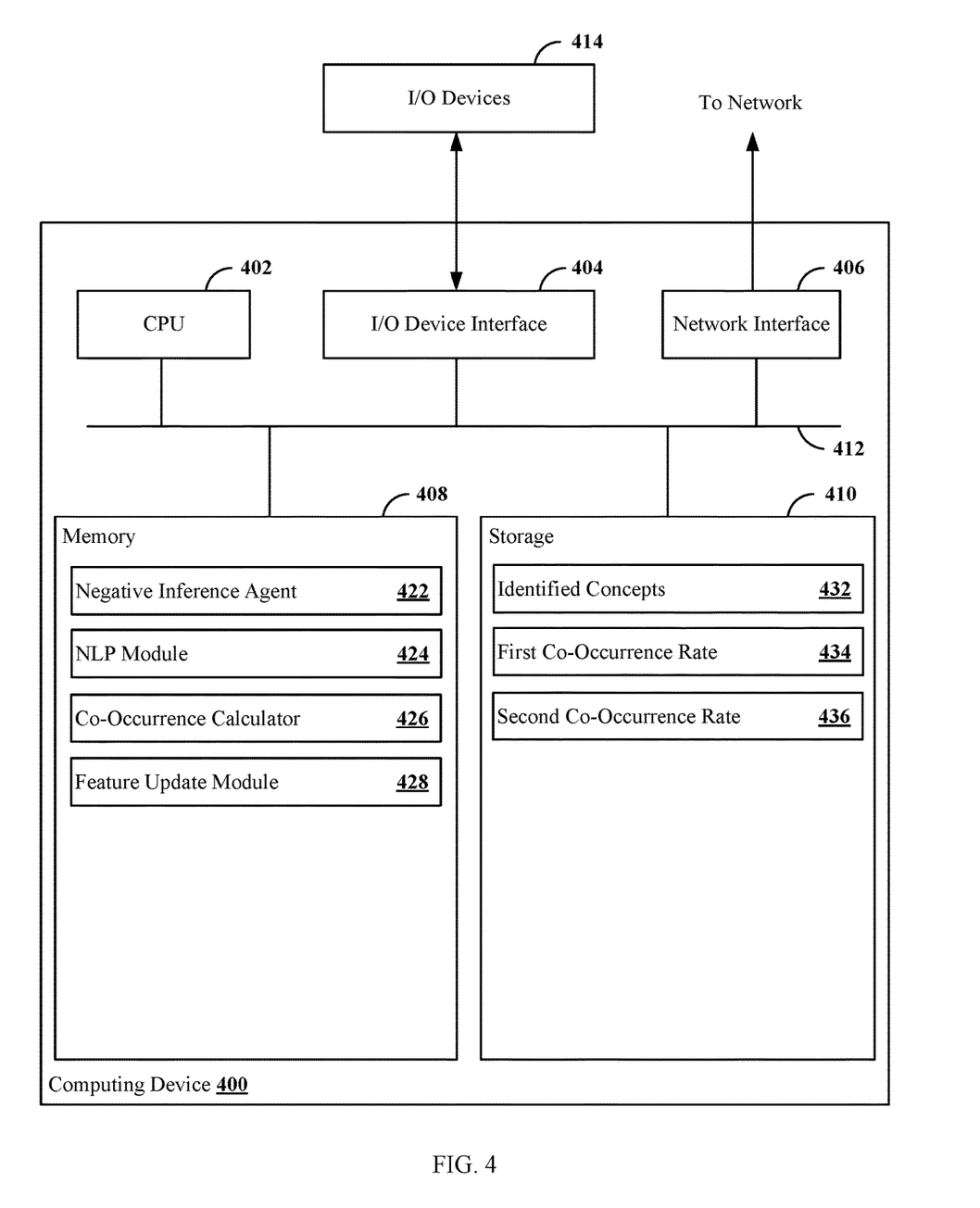
FIG. 4 is a block diagram of an example computing device for performing feature engineering including negative inferences.

FIG. 4 is a block diagram of an example computing device 400 for performing feature engineering. As shown, computing device 400 includes a central processing unit (CPU) 402, one or more input/output (I/O) device interfaces 404, which may allow for the connection of various I/O devices 414 (e.g., keyboards, displays, mouse devices, pen input, etc.) to the computing device 400.

CPU 402 may retrieve and execute programming instructions stored in memory 408. Similarly, CPU 402 may retrieve and store application data residing in memory 408. Interconnect 412 allows for transmission of programming instructions and application data, among CPU 402, I/O device interface 404, network interface 406, memory 408, and storage 410. CPU 402 is included to be representative of a single CPU, multiple CPUs, a single CPU having multiple processing cores, and the like.

I/O device interface 404 may provide an interface for capturing data from one or more input devices integrated into or connected to computing device 400, such as keyboards, mice, touchscreens, and so on. Memory 408 may represent a random access memory (RAM), while storage 410 may be a solid state drive, for example. Although shown as a single unit, storage 410 may be a combination of fixed and/or removable storage devices, such as fixed drives, removable memory cards, network attached storage (NAS), or cloud-based storage.

As shown, memory 408 includes negative inference agent 422, NLP module 424, co-occurrence calculator 426 and feature update module 428. Negative inference agent 422, NLP module 424, co-occurrence calculator 426 and feature update module 428 are software routines executed based on instructions which may be stored in the storage 410. Such instructions may be executed by the CPU 402. Computing device 400 also includes network interface 406, memory 408, storage 410, and interconnect 412.

As shown, storage 410 includes identified concepts 432, first co-occurrence rate 434 and second co-occurrence rate 436. In general, NLP module 424 identifies concepts within a corpus of documents (or within a knowledge graph) to generate identified concepts 432. Then, co-occurrence calculator 426, using a corpus of documents, determines first co-occurrence rate 434 between a first concept and a second concept, and determines second co-occurrence rate 436 between the second concept and a third concept. Based on comparing first co-occurrence rate 434 and second co-occurrence rate 436 to a predetermined threshold, negative inference agent 422 determines if an inverse relationship exists between the second concept and the third concept. If so, feature update module 428 updates a set of obtained features for machine learning training to include an indication of the inverse relationship.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the following, reference is made to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the foregoing is directed to embodiments of the present invention, other and further embodiments of the invention may be devised without departing from the basic scope thereof, and the scope thereof is determined by the claims that follow.

What is claimed is:

1. A method comprising:
   identifying a plurality of concepts;
   analyzing a corpus of documents to determine a first co-occurrence rate for a first concept and a second concept in the plurality of concepts,
   wherein the first co-occurrence rate is generated by determining how many times the first and second concepts were identified within a predefined proximity of each other in one or more documents of the corpus of documents;
   upon determining that the first co-occurrence rate exceeds a predefined threshold:
      determining that the first concept and the second concept are related;
      identifying a third concept that is also related to the first concept; and
      analyzing the corpus of documents to determine a second co-occurrence rate for the second concept and the third concept, comprising determining how many times the second and third concepts were identified within the predefined proximity of each other in one or more documents of the corpus of documents:
   upon determining that second co-occurrence rate is below the predefined threshold, determining an inverse relationship between the second concept and the third concept, wherein the inverse relationship indicates that the second and third concepts are inversely related;

generating test data for training a machine learning model including a negative inference between the second concept and the third concept, wherein the negative inference indicates that presence of the second concept requires absence of the third concept; and training the machine learning model using the test data, wherein the test data includes an indication that presence of the second concept rules out presence of the third concept.

2. The method of claim 1, further comprising determining the set of concepts related to the first concept, comprising analyzing a knowledge graph, wherein the knowledge graph includes the plurality of concepts and a plurality of identified connections among the plurality of concepts.

3. The method of claim 2, further comprising: updating the knowledge graph based on determining that the second concept and the third concept are inversely related.

4. The method of claim 3, wherein updating the knowledge graph comprises adding a negative connection between the second concept and the third concept in the knowledge graph.

5. The method of claim 1, wherein the first concept and the second concept are associated with medical conditions.

6. The method of claim 5, wherein the machine learning model is used to perform treatment selection for a patient based in part on medical conditions of the patient.

7. The method of claim 1, further comprising: upon determining that a first patient is associated with the second concept, determining that the first patient is not associated with the third concept.

8. A system, comprising:
a processor; and
a memory including computer readable instructions, which, when executed by the processor, cause the system to perform an operation comprising:
identifying a plurality of concepts;
analyzing a corpus of documents to determine a first co-occurrence rate for a first concept and a second concept in the plurality of concepts,
wherein the first co-occurrence rate is generated by determining how many times the first and second concepts were identified within a predefined proximity of each other in one or more documents of the corpus of documents;
upon determining that the first co-occurrence rate exceeds a predefined threshold:
determining that the first concept and the second concept are related;
identifying a third concept that is also related to the first concept; and
analyzing the corpus of documents to determine a second co-occurrence rate for the second concept and the third concept, comprising determining how many times the second and third concepts were identified within the predefined proximity of each other in one or more documents of the corpus of documents;
upon determining that second co-occurrence rate is below the predefined threshold, determining an inverse relationship between the second concept and the third concept, wherein the inverse relationship indicates that the second and third concepts are inversely related;
generating test data for training a machine learning model including a negative inference between the second concept and the third concept, wherein the negative inference indicates that presence of the second concept requires absence of the third concept; and training the machine learning model using the test data, wherein the test data includes an indication that presence of the second concept rules out presence of the third concept.

9. The system of claim 8, the operation further comprising:
upon determining that a first patient is associated with the second concept, determining that the first patient is not associated with the third concept.

10. The system of claim 9, wherein the first concept and the second concept are associated with medical conditions.

11. The system of claim 10, wherein the machine learning model is used to perform treatment selection for a patient based in part on medical conditions of the patient.

12. The system of claim 8, the operation further comprising determining the set of concepts related to the first concept comprises analyzing a knowledge graph, wherein the Knowledge graph includes the plurality of concepts and a plurality of identified connections among the plurality of concepts.

13. The system of claim 12, the operation further comprising:
updating the knowledge graph based on determining that the second concept and the third concept are inversely related.

14. The system of claim 13, wherein updating the knowledge graph comprises adding a negative connection between the second concept and the third concept in the knowledge graph.

15. A non-transitory computer readable medium comprising instructions, which when executed by a processor of a computing device, cause the computing device to perform an operation comprising:
identifying a plurality of concepts;
analyzing a corpus of documents to determine a first co-occurrence rate for a first concept and a second concept in the plurality of concepts, wherein the first co-occurrence rate is generated by determining how many times the first and second concepts were identified within a predefined proximity of each other in one or more documents of the corpus of documents;
upon determining that the first co-occurrence rate exceeds a predefined threshold:
determining that the first concept and the second concept are related:
identifying a third concept that is also related to the first concept; and
analyzing the corpus of documents to determine a second co-occurrence rate for the second concept and the third concept, comprising determining how many times the second and third concepts were identified within the predefined proximity of each other in one or more documents of the corpus of documents;
upon determining that second co-occurrence rate is below the predefined threshold, determining an inverse relationship between the second concept and the third concept, wherein the inverse relationship indicates that the second and third concepts are inversely related;
generating test data for training a machine learning model including a negative inference between the second concept and the third concept, wherein the negative inference indicates that presence of the second concept requires absence of the third concept; and training the machine learning model using the test data, wherein the test data includes an indication that presence of the second concept rules out presence of the third concept.

16. The non-transitory computer readable medium of claim 15, the operation further comprising determining the set of concepts related to the first concept comprises analyzing a Knowledge graph, wherein the knowledge graph includes the plurality of concepts and a plurality of identified connections among the plurality of concepts.

17. The non-transitory computer readable medium of claim 16, the operation further comprising: updating the knowledge graph based on determining that the second concept and the third concept are inversely related.

18. The non-transitory computer readable medium of claim 15, wherein the first concept and the second concept are associated with medical conditions.

19. The non-transitory computer readable medium of claim 18, wherein the machine learning model is used to perform treatment selection for a patient based in part on medical conditions of the patient.

20. The non-transitory computer readable medium of claim 15, the operation further comprising:
  upon determining that a first patient is associated with the second concept, determining that the first patient is not associated with the third concept.

* * * * *